(12) United States Patent
Takeshita et al.

(10) Patent No.: US 6,277,559 B2
(45) Date of Patent: Aug. 21, 2001

(54) HISTAMINE MEASURING APPARATUS AND A HISTAMINE MEASURING METHOD

(75) Inventors: Tomoko Takeshita, Higashimatsuyama; Jun Otomo, Tokyo, both of (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/788,361

(22) Filed: Feb. 21, 2001

Related U.S. Application Data

(62) Division of application No. 09/604,512, filed on Jun. 27, 2000.

(30) Foreign Application Priority Data

Jun. 30, 1999 (JP) .................................................. 11-184740

(51) Int. Cl.$^7$ ............................ C12Q 1/00; G01N 27/26; G01N 31/00; C07D 233/61; C12M 1/34

(52) U.S. Cl. ............................. 435/4; 435/7.1; 435/7.92; 435/13; 435/174; 435/283.1; 435/285.2; 435/286.7; 435/287.1; 435/287.2; 435/288.5; 435/288.7; 435/287.9; 435/808; 422/44; 422/530; 204/400; 204/403; 204/409; 204/408; 204/422; 436/18; 436/63; 436/147; 436/164; 436/172; 436/518; 436/543; 436/544; 436/545; 436/546; 436/805; 436/807; 436/826; 548/335.5

(58) Field of Search ................................. 204/400, 408, 204/409, 403, 422; 422/44, 530; 548/335.5; 435/4, 7.1, 7.92, 13, 174, 283.1, 285.2, 286.7, 287.1, 287.2, 288.5, 288.7, 287.9, 808; 436/18, 63, 147, 164, 172, 518, 543, 544, 545, 546, 805, 807, 826

(56) References Cited

U.S. PATENT DOCUMENTS 4,343,782 * 8/1982 Shapiro ..................................... 424/3
4,629,706 * 12/1986 Hammod et al. ..................... 436/513

(List continued on next page.)

FOREIGN PATENT DOCUMENTS

| 6-331619 | 12/1994 | (JP) . |
| 10-062415 | 3/1998 | (JP) . |
| 10-170514 | 6/1998 | (JP) . |
| 11-083785 | 3/1999 | (JP) . |

OTHER PUBLICATIONS

Darbon et al. Immunoelectrodes in Protein Detection: Comparison between Glassy Carbon and a Semimetallic Ni/P Thin Film as Binding Support. Anal. Chem. vol. 70, No. 23 (1998) pp. 5072–5078.*

(List continued on next page.)

*Primary Examiner*—Long V. Le
*Assistant Examiner*—Kartic Padmanabhan
(74) *Attorney, Agent, or Firm*—Mattingly, Stanger & Malur, P.C.

(57) ABSTRACT

Histamine may be quantitatively measured by performing the following steps. First, an oocyte that expresses histamine receptors is held in a recess formed at the bottom of a vessel. Then, first and second electrodes are inserted into the oocyte. Subsequently, the membrane potential of the oocyte is measured by using the first electrode to stabilize this membrane potential at a predetermined level by driving a current through the second electrode using circuitry for clamping the membrane potential of the oocyte. A sample is then infused into a fine reacting tube having an antigen immobilized on its inner surface together with some buffer solution to promote a histamine releasing reaction. The solution containing histamines that is released in the fine reacting tube is transferred to the vessel to make contact with the oocyte in the vessel. Finally, an electric response of the oocyte caused by the contact with the solution is detected and the concentration of the histamine released in the histamine releasing reaction in the fine reacting tube is determined. The entire blood or mast cell suspension may be used as a sample without pretreatment.

11 Claims, 5 Drawing Sheets

U.S. PATENT DOCUMENTS

| | | | |
|---|---|---|---|
| 5,098,831 | * | 3/1992 | Skov et al. .............................. 435/29 |
| 5,437,861 | * | 8/1995 | Okarma et al. ................... 424/78.08 |
| 5,460,945 | * | 10/1995 | Springer et al. .................... 435/7.24 |
| 5,468,650 | * | 11/1995 | Skov et al. ........................... 436/527 |
| 5,476,797 | * | 12/1995 | Matsunaga ........................... 436/513 |
| 5,565,329 | * | 10/1996 | Ohashi et al. ........................ 435/25 |
| 5,747,047 | * | 5/1998 | Oka et al. ......................... 424/275.1 |
| 5,849,719 | * | 12/1998 | Carson et al. .......................... 514/44 |
| 6,048,722 | * | 4/2000 | Farb et al. ........................ 435/287.1 |

OTHER PUBLICATIONS

Kusano et al. Cholinergic and catecholaminergic receptors in the Xenopus oocyte membrane, Journal of Physiology. vol. 328 (1982) pp. 143–170.*

SRL HOKAN, vol. 21, 1997, Histamine Release Test—Diagnosis of Allergies, K. Tabe, pp. 17–22.

* cited by examiner

BLOOD CONTAINING HISTAMINE

BLOOD NOT CONTAINING HISTAMINE (1) HEPARIN BLOOD COLLECTION

↓

(2) ADDTION OF ANTIGEN (3) HISTAMINE RELEASE 37°C, ~30MIN

↓

(4) COLLECTING WHOLE BLOOD STIMULATED BY ANTIGEN

↓

(5) ADDING COLLECTED WHOLE BLOOD TO XENOPUS OOCYTE

↓

(6) MEASURING ELECTRICAL RESPONSE OF XENOPUS OOCYTE

↓

(7) QUANTIFYING CONCENTRATION OF HISTAMINE

| SAMPLE NO. | B (nM) | A (nM) | C (nM) | α (%) |
|---|---|---|---|---|
| 1 | 1500 | 1155 | 525 | 42.0 |
| 2 | 1300 | <20 | <20 | ND |
| 3 | 600 | 1050 | <20 | 171.7 |
| 4 | 940 | <20 | <20 | ND |
| 5 | 860 | <20 | <20 | ND |

HISTAMINE MEASURING APPARATUS AND A HISTAMINE MEASURING METHOD

This is a divisional application of U.S. Ser. No. 09/604,512, filed Jun. 27, 2000.

BACKGROUND OF THE INVENTION

1. Field of the Invention

The present invention is directed to a histamine measuring apparatus and a histamine measuring method for quantitatively measuring histamine present in blood or mast cells suspensions.

2. Description of the Prior Art

A histamine releasing test is a quantitative analysis of to histamine extracellularly released by stimulating lewcocytes (white blood cells) in the blood or mast cells in the mucosa and promoting releasing histamine contained therein outside the cells. The histamine release test has been reported to be a method useful in identifying some allergens in some allergic disorders and diseases (c.f., Prior Art 1: Tabe, kazuaki: histamine release test—diagnosis of allergies, SRL HOKAN, vol 21, pp. 17–22 (1997).

The known measurements of freed histamine (histamine released in free state) includes, for example, a method using fluorescent HPLC (fluorescent high performance liquid chromatography) to purify the histamine to react it with a fluorescent reagent in order to measure the amount of fluorescence emitted from the fluorescent reagent reacted with the histamine (c.f. , Prior Art 2: Japanese Patent Laid-Open No. H6-331619), a method using glass fibers to purify the freed histamine to react it with a fluorescent reagent in order to measure the amount of fluorescence emitted from the fluorescent reagent coupled with the free histamine (c.f., Prior Art 3: Japanese Patent Laid-Open No. H10-170514, Japanese Patent Laid-Open No. 10-62415), competitive immunoassays commercially available from ICN Pharmaceuticals or Immunotech, and an ELISA (c.f., Prior Art 4).

SUMMARY OF THE INVENTION

In general, the measurement of histamine may require:

(1) direct analysis of histamine without using labeling thereof;

(2) direct quantitative measurement of histamine without pretreatment;

(3) quick delivery of results; and (4) specificity to the histamine.

Prior Art methodologies as have been described above are all indirect, quantitative measurement methods of histamine, which isolate the histamine from a sample, and label the isolated histamine with a fluorescent reagent to measure the labeled histamine reacted with a fluorescent reagent. All of the Prior Art methodologies requires complex pretreatment such as purification of samples, isolation of histamine, and labeling of histamine with a fluorescent reagent, and also requires for hours to obtain a quantitative results of histamine analysis.

The primary object of the present invention is in general to provide a histamine measuring apparatus and a histamine measuring method, which may satisfy the requirements listed above of histamine measurement.

In accordance with the histamine quantitative analyzing apparatus and method of the present invention, histamine quantitative analysis will be achieved by:

providing cells with histamine receptor being expressed;

adding a sample having been stimulated by an antigen to the cells expressing the receptor; and detecting the resulting electrical response of cells.

For example, a predetermined amount of antigen will be added to a sample of collected whole blood, the sample with antigen will be incubated for 10 to 30 minutes at 37° C. to promote an allergic reaction (antigen challenge) therebetween to release the histamine into the plasma. It may be preferable to gently shake the blood sample while promoting the allergic reaction. The period of time of reaction described here is indicated by way of example. The reaction time may vary depending on the optimized allergic reaction.

Examples of sample include, whole blood specimen, leucocytes in the blood, and mast cell suspensions in which the mast cells of mucosal tissue are cultured.

An allergic reaction may be invoked in general by the binding of an allergen with a corresponding IgE present in the cell membrane of cells contributing to the allergic reaction such as mast cells, basophils, in the sample blood. The binding may trigger a reaction of releasing a relevant chemical mediator (chemical transmitter) such as histamine in the cells contributing to the allergy reaction. In the description hereinbelow, the reaction of releasing histamine will be referred to as "histamine release (releasing) reaction."

The concentration (A) of histamine extracellularly released by the histamine releasing reaction may be determined by using a calibration curve thereof. The calibration curve may be obtained by stimulating cells with the histamine receptor preliminary expressed by means of a plurality of known concentrations of histamine to detect the cellular electric responses at respective concentration of histamine and may be expressed as a relation between a plurality of known concentrations of histamine and detected electric responses.

The ratio of histamine release α (%) may be determined by $$\alpha = 100 \times (A-V)/B$$

where B is a histamine concentration given by the quantitative measurement of histamine released from the sample after freezing and thawing the sample having stimulated by the antigen, C is a concentration of free histamine released in non stimulated state by adding some buffer solution instead of the antigen to the sample.

The concentration of released histamine (C) designates to a released histamine concentration by the stimulation with the buffer, which is so-called "concentration for the correction of background level".

The apparatus and method in accordance with the present invention allows the histamine released in the sample to be directly and quantitatively analyzed by using cells with histamine receptors expressed. The cells expressing histamine receptors may identify specifically and directly the histamine, even in case in which derivatives of histamine or histamine-like compounds are present in the sample, or in case in which there is a trace of histamine contained in the sample. The apparatus and method in accordance with the present invention, accordingly, may allow direct quantitative analysis of histamine to be performed in a shorter time, with no complex pretreatment of samples which may require long time.

An exemplary configuration of the present invention will be summarized below. The oocyte expressing the histamine receptors is held in the recess formed at the bottom of a vessel. A first electrode and a second electrode will be inserted into the oocyte to determine the membrane potential of oocyte by the first electrode, and then maintain the potential of oocyte membrane to a predetermined level by flowing electric current through the second electrode, by means of a circuitry for maintaining the potential of oocyte membrane. A sample will be flew through together with some buffer into a fine reacting tube with an antigen fixed on the inner surface of tube wall to promote the histamine releasing reaction. Thereafter the solution containing free histamine will be flew through a flowing tube into the vessel to make contact with the oocyte in the vessel. The electric response of the oocyte caused by the contact with the solution will be detected by the potential maintainer (clamping) circuit in order to determine the concentration of free histamine released by the histamine releasing reaction. The whole blood, or suspension may be used as the sample, without the need for any pretreatment.

In accordance with the present invention, the concentration of histamine may be determined in a shorter time, without the need for any pretreatment, so that the process steps for quantitative analysis, the number and amount of reagents may be reduced to minimum and the cost and the time needed for the measurement may be significantly saved.

In the following description an oocyte of Xenopus lavis (African clawed frog) will be used for the cell expressing the histamine receptors, by way of example. It should be understood that the present invention may be applicable by using any other types of cell.

Also in the following description of preferred embodiments, an exemplary case will be described in which the electric response of the cell with histamine receptors expressed will be detected by identifying histamine with the histamine receptors expressed on the cell membrane and by measuring the change in the membrane potential along with the open and close of chloride ion channel caused by the intracellular signal transduction. It is to be understood that the preferred embodiments described herein are presented and described for the purpose of illustrating the principle of the present invention and are not intended to be limiting. For example, it should be recognized that the present invention may be achieved by using the cellular response derived from the receptor stimulation of any other kinds such as those described in the Japanese Patent Laid-Open No. H11-083785 (Prior Art 5), or by using any other detecting methods.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

DETAILED DESCRIPTION OF THE PREFERRED EMBODIMENTS

Figure 1:
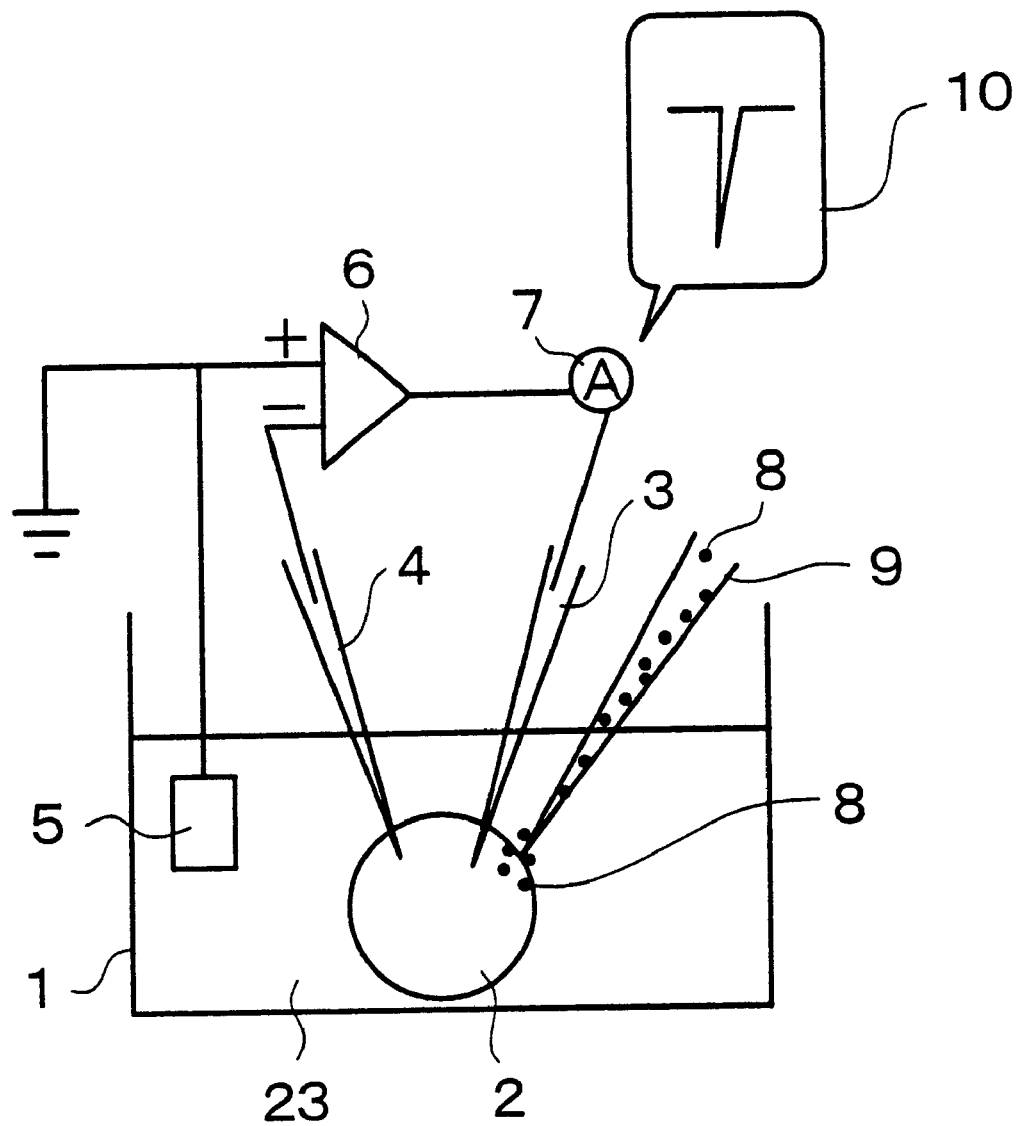
FIG. 1 shows a schematic diagram illustrating an apparatus in accordance with one preferred embodiment of the present invention, which is a histamine measuring apparatus for quantitatively analyzing the histamine by using the oocyte with histamine receptors expressed.

In the following description of the preferred embodiments, the histamine measuring apparatus and the histamine measuring method in accordance with the present invention will be described in greater details with reference to the quantitative analysis of histamine in the whole blood sample by using the oocyte with histamine receptors expressed.

A whole blood sample stimulated by the antigen will be added to the oocyte with histamine receptor expressed to detect the resulting electric response of the oocyte. A predetermined amount of antigen will be added to the collected whole blood sample (some buffer may be introduced if the whole blood sample is too viscous), and the whole blood sample and the antigen will be incubated at a temperature ranging from 30° C. to 45° C. for 10 to 30 minutes for promoting the allergy reaction therebetween in order to release histamine into the plasma.

The concentration of histamine (A) released into the plasma from the blood cells in the sample caused by the histamine releasing reaction may be determined by means of a calibration curve. The calibration curve may be obtained by stimulating cells with the histamine receptor preliminary expressed by means of a plurality of known concentrations of histamine to detect the cellular electric responses at respective concentration of histamine and may be expressed as a relation between a plurality of known concentrations of histamine and detected electric responses.

The ratio of histamine release $\alpha$ (%) may be determined by $$\alpha = 100 \times (A-C)/B$$

where B is a histamine concentration given by the quantitative measurement of histamine released from the cells in the sample blood after freezing and thawing the sample stimulated by the antigen, C is a concentration of released histamine in non stimulated state by adding some buffer instead of the antigen into the blood sample.

The concentration of released histamine in non-stimulation C designates to the concentration of free histamine released by the stimulation of buffer, i.e., so-called "concentration of correction of background".

The histamine analysis as have been described above may be carried out within approximately 20 to 50 minutes, including the calibration measurement for determining the calibration curve to be used. In case in which the calibration curve has been determined in advance, then the histamine measurement will be completed at most in 30 seconds for each sample.

In this preferred embodiment of the apparatus and method in accordance with the present invention, quantitative measurement of histamine released from the cells in the whole blood to the plasma may be directly carried out. If the histamine derivatives or histamine-like compounds are present in the cells or plasma of whole blood sample, or if the amount of histamine to be released into the plasma from the cells of whole blood is very low, the oocyte with histamine receptors expressed will specifically and directly identify the histamine. Accordingly the apparatus and method for measuring histamine in accordance with the present invention may directly and quantitatively analyze the released histamine from the whole blood cells to the plasma without the need for any pretreatment of whole blood sample.

Since the apparatus and method of the preferred embodiment in accordance with the present invention may detect the histamine by using the oocyte with histamine receptors expressed, the electric response of the oocyte caused by the physiological reaction induced at the time when the oocyte identifies the presence of histamine may be directly detected as an electric signal. The physiological reaction of oocyte is known to be occurred within milliseconds, thus the time required for detecting the histamine may be within one second.

The apparatus and method for measuring histamine of the preferred embodiment in accordance with the present invention may perform a quantitative measurement in significantly shorter time than any other Prior Art techniques requiring at least one hour for the analysis.

A detailed description of some preferred embodiments embodying the present invention will now be given referring to the accompanying drawings.

FIG. 1 shows a schematic diagram illustrating an apparatus in accordance with one preferred embodiment of the present invention, which is a histamine measuring apparatus for quantitatively analyzing the histamine by using the oocyte with histamine receptors expressed;

In this embodiment the oocyte of *Xenopus lavis* (African Clawed Frog) will be used. The unfertilized oocytes (eggs) of Xenopus lavis are subjected to be injected mRNA of histamine receptor. These oocytes will be incubated for two or three days in a culture medium so as to cause histamine receptors to be expressed. The histamine receptors will be active within the cell membrane of oocyte. When histamine binds to the histamine receptors, the information will be transferred inside the oocyte through the mediator (second messenger) already present in the oocyte.

As the result of a plurality of chemical mediation inside the oocyte, intracellular calcium ions are raised in the oocyte, opening the chloride ion channel of the oocyte cell membrane. This reaction will cause the change in potential of cell membrane inside and outside the oocyte.

In the present preferred embodiment of the present invention the change in the electric response of oocyte before and after the binding of histamine to the histamine receptors, namely, the change in potentials between the inside and the outside of oocyte cell membrane, will be detected as the change in electric current response.

In the present preferred embodiment of the present invention a method of whole cell clamp will be used in which a feedback circuitry will be used, which may flow current through the oocyte in the direction of suppressing the difference of membrane potential at the moment of change in potential of membrane of oocyte to maintain the potential to a predetermined constant holding potential.

As shown in FIG. 1, at the recess 16 (not shown) at the bottom of a vessel 1 fulfilled with buffer solution 23 for the oocyte, an oocyte 2 with the histamine receptors expressed will be held. The fine tips of glass electrodes 3 and 4, filled with KCl of 3 mole. and containing an Ag wire coated with AgCl will be inserted into the oocyte 2. After the insertion, each of the tips of glass electrodes 3 and 4 will be fixedly held by is an apparatus for holding electrodes, which is not shown in FIG. 1, but is provided correspondingly for respective electrode.

The potential of the glass electrode 3 will be transmitted to the differential amplifier 6 and the recorder 7 and recorded therein as the difference in potential to an external electrode 5. The glass electrode 3 may be an electrode for measuring the potential in the membrane of oocyte, while the glass electrode 4 may be used for maintaining the membrane potential of the oocyte to a predetermined constant level of –60 mV.

The differential amplifier 6 will apply the differential current between the signal transferred from the glass electrode 3 to the differential amplifier 6 and the holding potential in the whole cell clamping method to the oocyte 2 through the glass electrode 4. in this manner, when the histamine 8 will be dropped onto the oocyte 2 with the potential of cell membrane held at a constant level of –60 mV, by means of for example a micro-syringe or a pipette 9, the electric response (current response 10) of the oocyte 2 may be obtained. The current response 10 will be described in greater details below.

Figure 2:
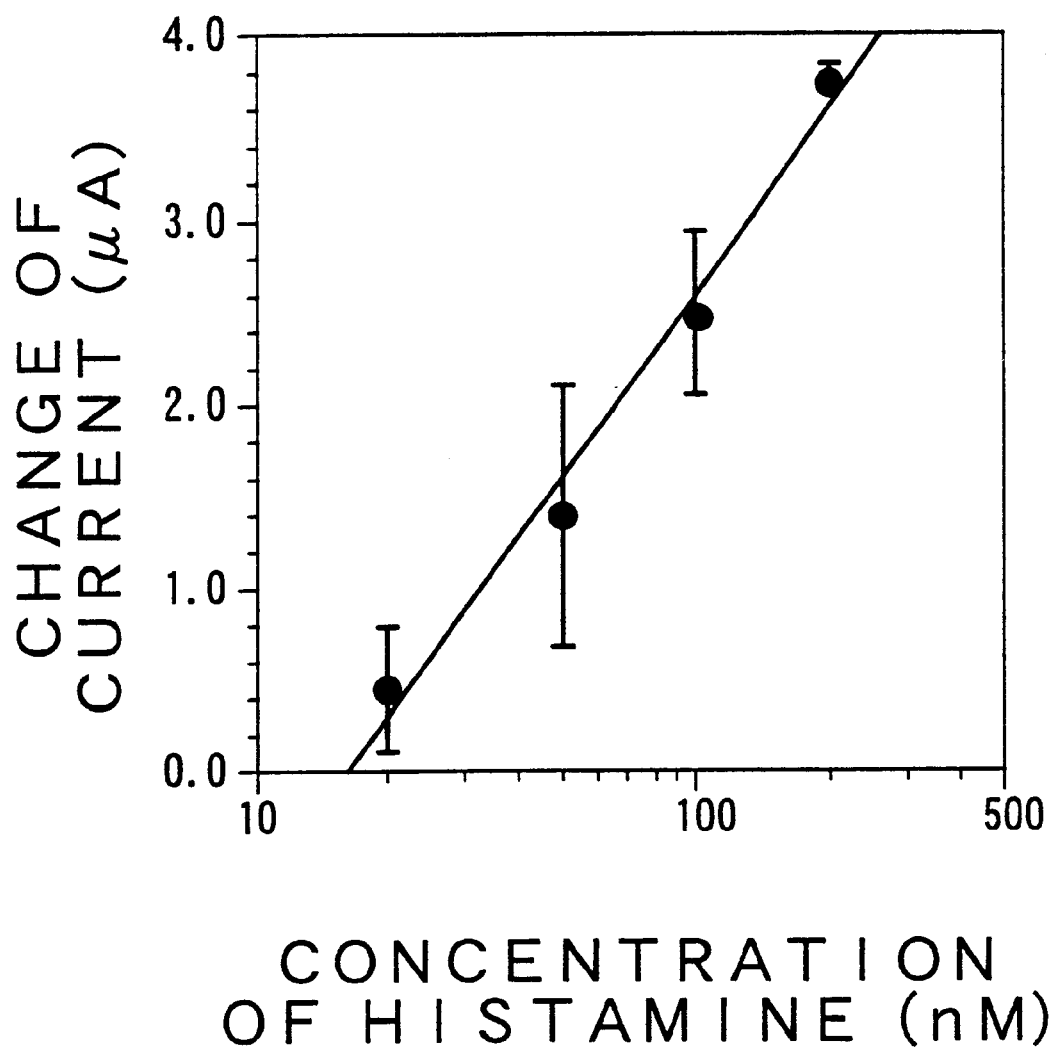
FIG. 2 shows a schematic diagram illustrating an exemplary analysis of histamine concentration and electric response of the oocyte both obtained by the apparatus shown in FIG. 1.

FIG. 2 shows a schematic diagram illustrating an exemplary analysis of histamine concentration and electric response of the oocyte both obtained by the apparatus shown in FIG. 1. The abscissa is the known concentration of histamine (nM) of the samples. The ordinate is the amount of change in potential between the inside and outside of the oocyte before and after the binding of histamine to the histamine receptors, measured as the change of current ($\mu$A).

As shown in FIG. 2, it is clear that the current change is in positive correlation with the concentration of histamine in the range of histamine concentration from 20 nM to 200 nM. This correlation (calibration curve) may be used for measuring a sample containing histamine at an unknown concentration by using the apparatus of the present invention shown in FIG. 1 so as to determine the unknown concentration of histamine.

Figure 3A:
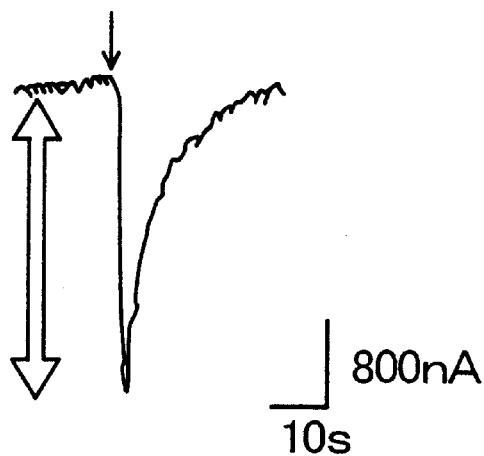
FIG. 3A shows a schematic diagram illustrating an exemplary analysis of electric response of oocyte, induced by the blood sample containing histamine, and obtained by using the apparatus shown in FIG. 1.
Figure 3B:
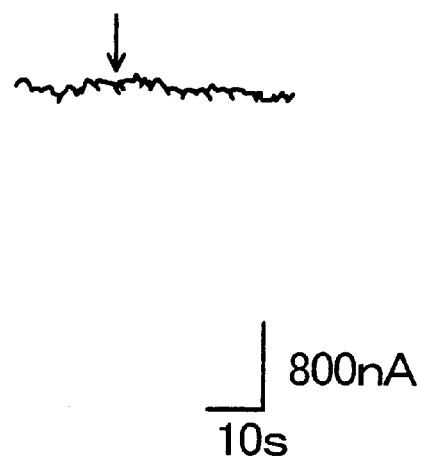
FIG. 3B shows a schematic diagram illustrating an exemplary analysis of electric response of oocyte, induced by the blood sample containing no histamine, and obtained by using the apparatus shown in FIG. 1.

FIG. 3A and FIG. 3B show schematic diagrams illustrating an exemplary analysis of electric current response of the oocyte, induced by the whole blood sample containing histamine (FIG. 3A) and by the blood sample containing no histamine (FIG. 3B) and obtained by using the apparatus shown in FIG. 1.

As shown in FIG. 3A, when at the moment as shown by the vertical arrow, the whole blood sample containing histamine is added to the oocyte expressing histamine receptors, the current response will be reached at the maximum value within one second, then will decrease gradually together with the elapsed time to disappear approximately 30 seconds after.

On the other hand, as shown in FIG. 3B, when the whole blood sample containing no histamine is added to the oocyte expressing histamine receptors at the moment as shown by the vertical arrow, no change in current response will be observed. This indicates that the change in current response as shown in FIG. 3A is based on the reaction between the histamine and histamine receptors, rather than the change of response caused by the impurity of whole blood sample. When applying the maximum value of the current response shown in FIG. 3A to the correlation (calibration curve) shown in FIG. 2, it can be seen that this maximum value of the current response may be caused by the histamine of concentration of approximately 100 nM. The outlined vertical arrow shown in FIG. 3A indicates the change in current before and after adding a whole blood sample containing histamine to the oocyte expressing histamine receptors.

As can be seen from the foregoing description, in accordance with the present invention, a whole blood sample may be used for quantitative analysis of histamine without needs for isolation, generator and labeling. As have been described above, by measuring the change in membrane potential as the change in current passing therethrough, along with the opening and closing of chloride ion channel caused by intracellular chemical mediator after identifying histamine by an oocyte expressing histamine receptors, the measurements for quantitative analysis of histamine may be obtained within one second after the oocyte identifies histamine.

EMBODIMENTS

[first embodiment]

By stimulating oocytes expressing histamine receptors with a plurality of known concentrations of histamine to detect the change in current as have been described above, the correlation (calibration curve) between the change in current and the concentrations of histamine as shown in FIG. 2 may be predetermined.

Figure 4:
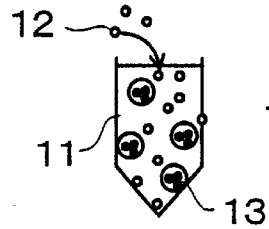
FIG. 4 shows a protocol of histamine analysis method in accordance with a preferred embodiment of the present invention.
Figure 4:
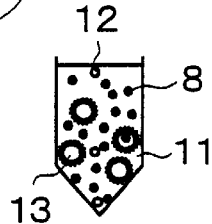

FIG. 4 shows a protocol of histamine analysis method in accordance with a preferred embodiment of the present invention. The protocol will be described below in greater details with reference to FIG. 4:

(1) A whole blood sample 11 will be collected from vein of a human elbow, using heparin as anticoagulant.

(2) A predetermined amount of antigen 12 such as cedar pollen will be added to the collected whole blood sample 11.

(3) The whole blood sample 11 will be incubated for approximately 30 minutes at 37° C. to promote histamine releasing reaction between the whole blood and antigen. Due to the allergy reaction basophils 13 in the whole blood sample will be stimulated and will release histamine 8;

(4) The whole blood sample 11 having stimulated by the antigen 12 will be sampled by means of a microsyringe or a pipette.

(5) The sample will be added to the oocyte expressing histamine receptors.

(6) The change in electric response of the oocyte will be measured by means of the apparatus shown in FIG. 1 to determine the change in current as have been described above.

(7) From the current change value, the concentration of histamine (A) in the whole blood sample 11 having stimulated by the antigen 12 may be determined by referring to the predetermined correlation (calibration curve).

The releasing rate of histamine α (%) may be determined by $$\alpha = 100 \times (A-C)/B$$

where B is a histamine concentration given by the quantitative measurement of histamine released from the cells in the sample whole blood after freezing and thawing the sample having stimulated by the antigen, C is a concentration of free released histamine in non stimulated state by adding the buffer solution 23 instead of the antigen into the blood sample.

The concentration of free histamine released in non-stimulation C designates to the concentration of free histamine released by the stimulation of buffer, i-e., so-called "concentration of correction of background".

The time required for a quantitative analysis of histamine in accordance with the first preferred embodiment will be approximately 30 minutes, which is significantly faster when compared with 3 hours needed for the method described in the Prior Art 3 above and 4 hours needed for the method described in the Prior Art 4 above, resulting in a saving of time.

The procedure of the method of measuring histamine in accordance with the first preferred embodiment of the present invention is characterized in that the collected sample may be used for quantitative analysis without need of any pretreatment of whole blood, with significantly fewer steps of processing as compared with any of Prior Art. The procedure of the method in accordance with the present invention requires only histamine of known concentration at the time of making a calibration curve, and no other reagents are needed, allowing the analytical cost to be reduced.

[second embodiment]

Figures 5, 6:
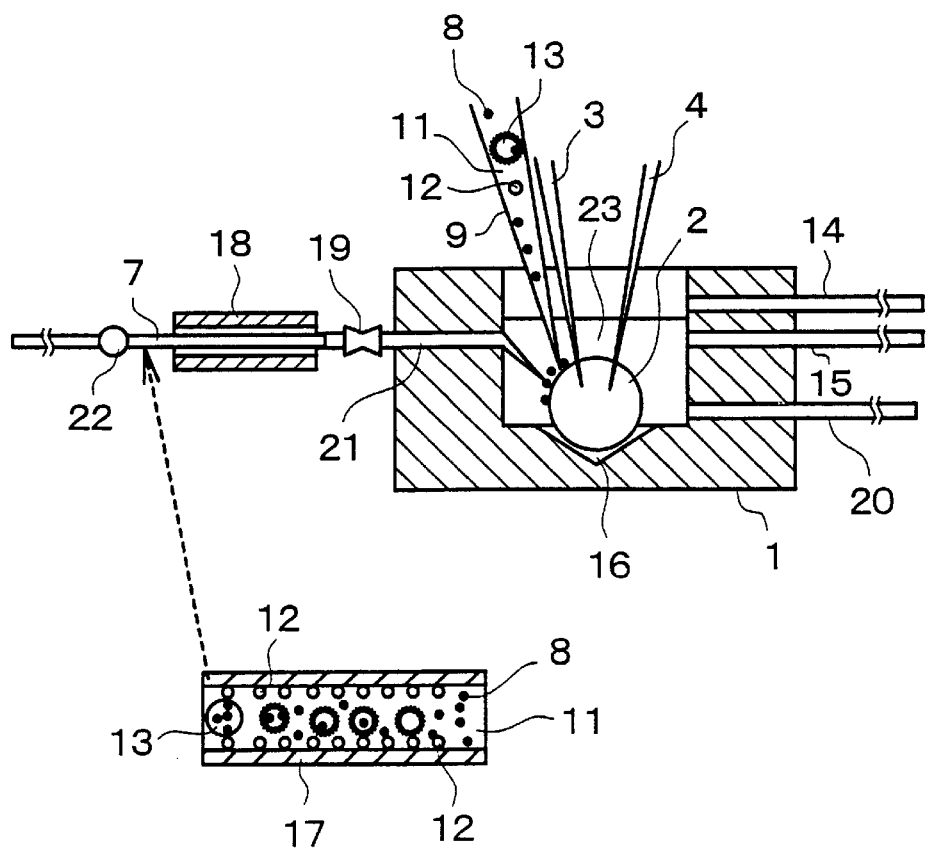
FIG. 5 shows a result of histamine analysis using a whole blood sample, obtained by using the apparatus shown in FIG. 1.
FIG. 6 shows a schematic diagram of an apparatus for measuring histamine in accordance with another preferred embodiment of the present invention, illustrating the overview of apparatus for quantitatively analyzing histamine by using the oocyte with histamine receptors expressed and a whole blood sample.

FIG. 5 shows an example of results of histamine analysis using whole blood samples (5 samples), obtained by using the apparatus shown in FIG. 1. The cedar pollen was used as antigen. FIG. 5 shows the results of measurement of histamine, A (concentrations of histamine in the whole blood samples stimulated by the cedar pollen), B (concentrations of histamine quantitatively determined from the histamine released from the cells of whole blood samples by freezing and thawing the whole blood samples stimulated by the cedar pollen) C (concentrations of freely released histamine in non stimulated state derived from the cells in the whole blood sample by adding the buffer solution 23 thereto instead of the cedar pollen antigen) and α (%) (histamine releasing rate), each determined for respective sample in accordance with the procedure similar to that of the first embodiment as have been described above.

In the histamine-releasing test in general with respect to blood samples, when the histamine-releasing rate of a sample is higher than or equal to 10% when stimulating with a specific allergen, the sample may be considered to be positive in the allergy reaction. In the exemplary embodiment shown in FIG. 5, the samples 1 and 3 are to be considered that the allergy reaction for the cedar pollen has been occurred. These results were consistent with the results of conventional HRT (Histamine Release Test) method as well as the subjective symptom or examinees.

[third embodiment]

FIG. 6 shows a schematic diagram of an apparatus for measuring histamine in accordance with another preferred embodiment of the present invention, illustrating the overview of an apparatus for quantitatively analyzing histamine by using the oocyte with histamine receptors expressed and a whole blood sample.

The apparatus shown in FIG. 6 is consisted of, in addition to the components of the apparatus shown in FIG. 1, a pouring tube 14 for pouring the buffer solution 23 into the vessel 1 with the assistance of a pump and the like, a draining tube 15 for draining excessive buffer solution 23 from the vessel 1 with the assistance of a pump and the like, and a draining tube 20 for purging the solution contained in the vessel 1 with the assistance of a pump and the like each time when the histamine analysis of a sample is completed. It should be noted that in FIG. 6 the external electrode 5, the differential amplifier 6, the grounding wire of differential amplifier 6, the recorder 7, the electric response of oocyte 10 are omitted for the sake of simplification.

The buffer solution 23 for oocyte 2 will be infused to the vessel 1 through the pouring tube 14 in excess of the liquid level detector portion of liquid level meter (not shown in FIG. 6) disposed inside the vessel. Then the driving apparatus of drain pump will be driven based on the output from the level detector until the level of buffer 23 will reach to the level of the level detector sensing portion in order to drain the excessive buffer solution 23 from the vessel 1 through the draining tube 15.

Thereafter, if for some reason or another the level of buffer solution 23 contained in the vessel 1 is decreased or increased, the decrease of buffer solution 23 will be detected by the level detector sensor portion and the driving apparatus of drain pump will be driven in accordance with the output of the level detector to automatically add an amount of buffer solution 23 through the pouring tube 14 into the vessel 1 in order to maintain the level of buffer solution 23 at a predetermined level. In this manner a predetermined constant amount of buffer solution 23 sufficient for dipping the oocyte 2 will be held in the vessel 1.

As shown in FIG. 6, in the recess 16 at the bottom of the vessel 1 filled with the buffer solution 23 for oocyte 2, a Xenopus oocyte expressing histamine receptors 2 will be immersed in a static manner. As similar to the apparatus shown in FIG. 1, the fine tips of glass electrode 3 and glass electrode 4 will be inserted into the Xenopus oocyte 2. The potential appeared in the glass electrode 3 will be transmitted to the differential amplifier 6 not shown in FIG. 6 as the differential potential from the external electrode 5. The differential amplifier 6 receiving the potential signaled from the glass electrode 3 will generate the current difference between the glass electrode 3 signal and the fixed potential in the whole cell clamping method and apply it to the Xenopus oocyte 2 through the glass electrode 4. The membrane potential of the oocyte will be accordingly held at a predetermined constant level of −60 mV.

Then the whole blood sample 11 prepared in accordance with the procedure shown in FIG. 4 will be added gently over the Xenopus oocyte 2 the membrane potential of which is held at −60 mV by means of an instrument such as micro-syringe or pipette 9. The whole blood sample 11 added to the vessel over the oocyte contains the histamine 8 released by the histamine releasing reaction, antigens 12, basophils 13, plasma and the like. The change of current before and after the histamine 8 is bound to the histamine receptors will be measured. As have been described in the foregoing discussion, the concentration of histamine 8 released from the cells in the whole blood may be determined from the change of current by predetermining a calibration curve.

Another configuration of apparatus for adding the prepared whole blood sample 11 over the Xenopus oocyte 2 without using a micro-syringe or pipette 9 will be described below in greater details. As shown in FIG. 6, a fine reacting tube (glass capillary) 17 may be provided to the apparatus for carrying out therein the histamine releasing reaction in the whole blood sample, such that step (3) of the procedure shown in FIG. 4 will be completed within the fine reacting tube 17. On the inner surface of the fine reacting tube 17 the antigen 12 such as cedar pollen and the like are immobilized.

A temperature controlling device (heater) 18 configured so as to surround the outer surface of tubing wall of the fine reacting tube 17 will control the temperature of fine reacting tube 17 at a temperature ranging from 30° C. to 45° C. for promoting the histamine releasing reaction. 5 to 20 mL of whole blood sample will be directly poured into the fine reacting tube 17 held at 37° C. via the tubing of left hand side of a cock 22 in the figure and the sample will be held therein for 30 minutes to initiate and promote the histamine releasing reaction.

Once the histamine releasing reaction in the fine reacting tube 17 has been completed, the temperature inside the fine reacting tube 17 will be decreased back to the room temperature and then a cock 19 will be opened so that the blood sample solution containing the histamine 8 released by the histamine releasing reaction, antigen 12, basophils 13, plasma and the like will be transferred to the surface of the Xenopus oocyte 2 held at the recess 16 of the bottom of vessel 1 through the cock 19 and flowing tube 21. Through the fine tip of the flowing tube 21, the solution containing histamine 8 and the like will be added over the Xenopus oocyte 2. After transfer the cock 19 may be closed.

The cross-sectional form of the flowing tube 21 is round and the tube 21 is bent at the proximity of its tip. The flowing tube 21 will be inserted to an opening provided on the sidewall of the vessel 1 in round cross-sectional shape. The axis of the opening aligns to the projection line extendingly projected to the bottom of vessel 1, the axis passing through the center of recess 16. The flowing tube 21 may be movable in rotative and translatory manner within the opening. The relative position of the tip of flowing tube 21 with the surface of oocyte held on the recess 16 may be adjusted by moving the flowing tube 21 in rotative or translatory direction as described above.

After the adjustment of relative position, the sample solution containing the histamine 8, antigen 12, basophils 13, plasma and the like will be gently add the Xenopus oocyte 2 having the membrane potential held at −60 mV by controllably flowing the buffer solution 23 or sterile gas from the tubing of left hand side of the cock 22 with the flow rate being controlled.

As have been described above, by measuring the change in current before and after the histamine 8 is bound to the histamine receptors of oocyte and using the predefined calibration curve, the concentration of histamine 8 released from the cells in the whole blood sample may be determined.

When the measurement of change in current has been completed, the glass electrodes 3 and 4 may be drawn from the oocyte, and the solution in the vessel 1 together with the oocyte may be drained through the draining tube 20 by for example suction by means of a purge pump. Then the electrodes 3 and 4 may be moved in one side of recess on which the oocyte will be held. Some washing solution may be poured into the vessel 1 through the pouring tube 14 to stir washing solution with a stirrer not shown in the figure in the vessel 1 to wash and rinse the vessel and thereafter the washing solution may be drained through the draining tube 20. The above washing process will be repeated three to four times to complete washing step of the vessel.

Then, by opening the cock 19 to flow washing solution through the tubing of left hand side of the cock 22 for several times to wash and rinse the inside of the fine reacting tube 17, cock 19, and flowing tube 21. Finally, the above washing process will be iterated for several times to complete washing step of the apparatus. In the configuration using the fine reacting tube 17, the quantitative analysis of the concentration of histamine released from the cells in the whole blood sample along with the histamine releasing reaction of whole blood may be continuously carried out. More specifically, the sequential change of histamine releasing process may be allowed to measure in a contiguous manner. In such a case the relative position of the fine tip of flowing tube 21 and the oocyte held in the recess 16 should be controlled by the rotative and translative displacement as have been described above prior to analysis.

Then the sample will be directly injected through the tubing of left hand side of the cock 22 to the fine reacting tube 17 having the antigen 12 such as cedar pollen immobilized on the surface of inner wall thereof and held by the temperature controlling device (heater) 18 at a temperature in a range from 30° C. to 45° C. for promoting the histamine releasing reaction. Immediately after that, the cock 19 will be opened to flow the buffer solution 23 held at a temperature approximately same to that of the fine reacting tube 17 at slower rate through the tubing of left hand side of the cock 22.

A membrane having a number of micropores through which the histamine 8 may be passed but the basophils 13 may not be provided for example between the fine reacting tube 17 and the cock 19.

Although the present invention has been described in conjunction with several preferred embodiments thereof, it should be understood that these embodiments are disclosed by way of examples and the present invention is not to be limited thereto. It should be recognized that many changes and modifications may be made by those skilled in the art without departing from the true spirit and the scope of the present invention according to the appended claims.

What is claimed is:

1. A histamine measuring method for quantitatively analyzing a concentration of histamine, comprising the steps of:

preparing an oocyte which expresses histamine receptors and identifies specifically the presence of histamine;

holding said oocyte in a recess at a bottom of a vessel in which a buffer solution is filled;

inserting first and second electrodes into said oocyte held in the recess;

measuring a potential of a membrane of said oocyte by means of said first electrode inserted into said oocyte held in the recess, and maintaining the potential of the membrane of said oocyte held in the recess at a constant potential by applying a current through said second electrode inserted into said oocyte held in the recess;

infusing a sample into a fine reacting tube having an antigen immobilized on an inner surface thereof wherein said antigen stimulates histamine release from the sample infused into said fine reacting tube;

transferring a solution containing histamine released from the sample in said fine reacting tube to said vessel to make contact with said oocyte in said vessel;

detecting a change in an electric response of said oocyte before and after binding of histamine to the histamine receptors; and determining a concentration of histamine released from the sample in said fine reacting tube.

2. A histamine measuring method according to claim 1, wherein said sample is a whole blood sample without pretreatment or a mast cell suspension without pretreatment.

3. A histamine measuring method according to claim 1, further comprising the step of:

controlling a temperature of said fine reacting tube at a temperature ranging from 30° C. to 45° C. to promote release of histamine from the sample.

4. A histamine measuring method according to claim 1, further comprising the step of:

determining the concentration (A) of histamine released from the sample in said fine reacting tube by means of a predefined calibration curve obtained by stimulating said oocyte with a plurality of known concentrations of histamine to detect the electric response of said oocyte to obtain a correlation between said electric responses and said plurality of known concentrations of histamine.

5. A histamine measuring method according to claim 4, further comprising the step of:

determining a histamine releasing rate given by (A−C)/B where B is a histamine concentration given by a quantitative measurement of histamine contained in cells in said sample and released by freezing and thawing the sample stimulated by the antigen, C is a concentration of free histamine released from the sample without stimulation after adding some buffer solution instead of the antigen into the sample.

6. A histamine measuring method according to claim 1, wherein said oocyte is an unfertilized oocyte of *Xenopus lavis*.

7. A histamine measuring method for quantitatively analyzing a concentration of histamine, comprising the steps of:

preparing a cell which expresses histamine receptors and identifies specifically the presence of histamine;

holding said cell in a recess at a bottom of a vessel in which a buffer solution is filled;

inserting first and second electrodes into said cell held in the recess;

measuring a potential of a membrane of said cell by means of said first electrode inserted into said cell held in the recess, and maintaining the potential of the membrane of said cell held in the recess at a constant potential by applying a current through said second electrode inserted into said cell held in the recess;

infusing a sample into a fine reacting tube having an antigen immobilized on an inner surface thereof wherein said antigen stimulates histamine release from the sample infused into said fine reacting tube;

transferring a solution containing histamine released from the sample in said fine reacting tube to said vessel to make contact with said cell in said vessel;

detecting a change in an electric response of said cell before and after binding of histamine to the histamine receptors; and determining a concentration of histamine released from the sample in said fine reacting tube.

8. A histamine measuring method according to claim 7, wherein said cell is an oocyte and said antigen is a cedar pollen.

9. A histamine measuring method according to claim 8, wherein said oocyte is an unfertilized oocyte of *Xenopus lavis*.

10. A histamine measuring method according to claim 7, wherein the sample is whole blood, leukocytes in blood, or a mast cell suspension.

11. A histamine measuring method according to claim 7, further comprising the step of:

controlling a temperature of said fine reacting tube at a temperature ranging from 30° C. to 45° C. to promote release of histamine from the sample.

* * * * *